(12) United States Patent
Bombardini

(10) Patent No.: US 6,859,662 B2
(45) Date of Patent: Feb. 22, 2005

(54) METHOD AND DEVICE FOR THE DIAGNOSIS AND THERAPY OF CHRONIC HEART FAILURE

(76) Inventor: Tonino Bombardini, Via Amendola, 43, Imola, Bologna (IT), 40026

( * ) Notice: Subject to any disclaimer, the term of this patent is extended or adjusted under 35 U.S.C. 154(b) by 426 days.

(21) Appl. No.: 10/023,761

(22) Filed: Dec. 21, 2001

(65) Prior Publication Data

US 2002/0091332 A1 Jul. 11, 2002

(30) Foreign Application Priority Data

Dec. 21, 2000 (IT) ..................................... RE2000A0134

(51) Int. Cl.$^7$ ................................................ A61B 5/04
(52) U.S. Cl. ......................... 600/510; 600/513; 607/24
(58) Field of Search ................................ 600/508–510, 600/453, 513; 607/9, 23, 24

(56) References Cited

U.S. PATENT DOCUMENTS 5,178,154 A  1/1993  Ackmann et al.
5,370,122 A  12/1994 Kunig et al.
5,584,298 A  12/1996 Kabal
6,336,903 B1 * 1/2002 Bardy ..................... 600/508

FOREIGN PATENT DOCUMENTS

EP  0 651 970 A1  5/1995
WO  WO 98/51211  11/1998
WO  WO 99/12468  3/1999

* cited by examiner

*Primary Examiner*—Angela D. Sykes
*Assistant Examiner*—Roderick Bradford
(74) *Attorney, Agent, or Firm*—Browdy and Neimark, P.L.L.C.

(57) ABSTRACT

Method and device for the diagnosis and therapy of chronic heart failure comprising continuous monitoring of the patient and continuous determination of significant decompensation parameters during a sample period of normal patient life, recording the data determined, continuously monitoring these data during therapy, comparing the memorized data with those determined during the same time span of the sample period and comparing the duration of periods in which decompensation is present with the total duration of those periods during which decompensation is absent or conforms to that determined during the sample period.

15 Claims, 6 Drawing Sheets

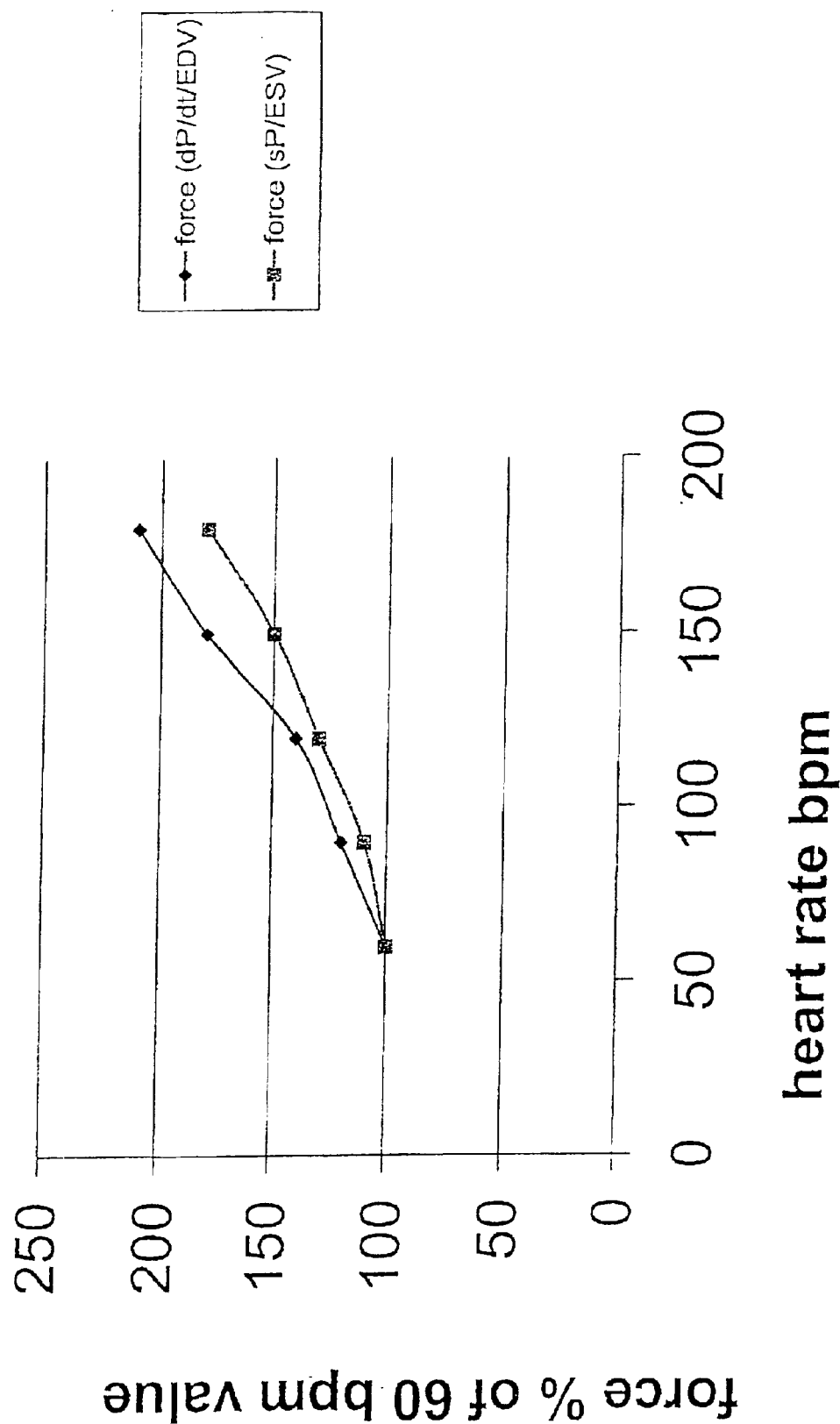

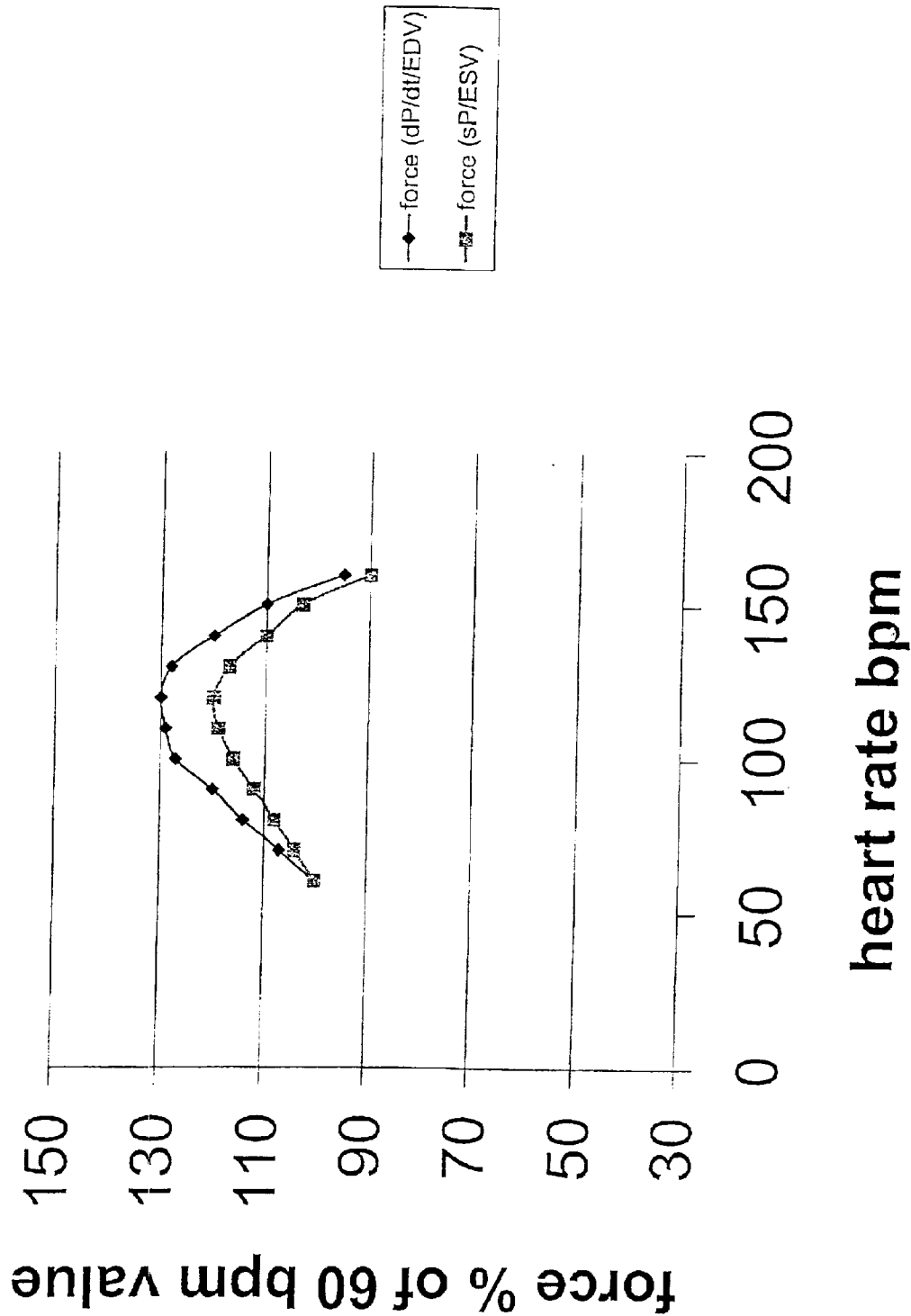

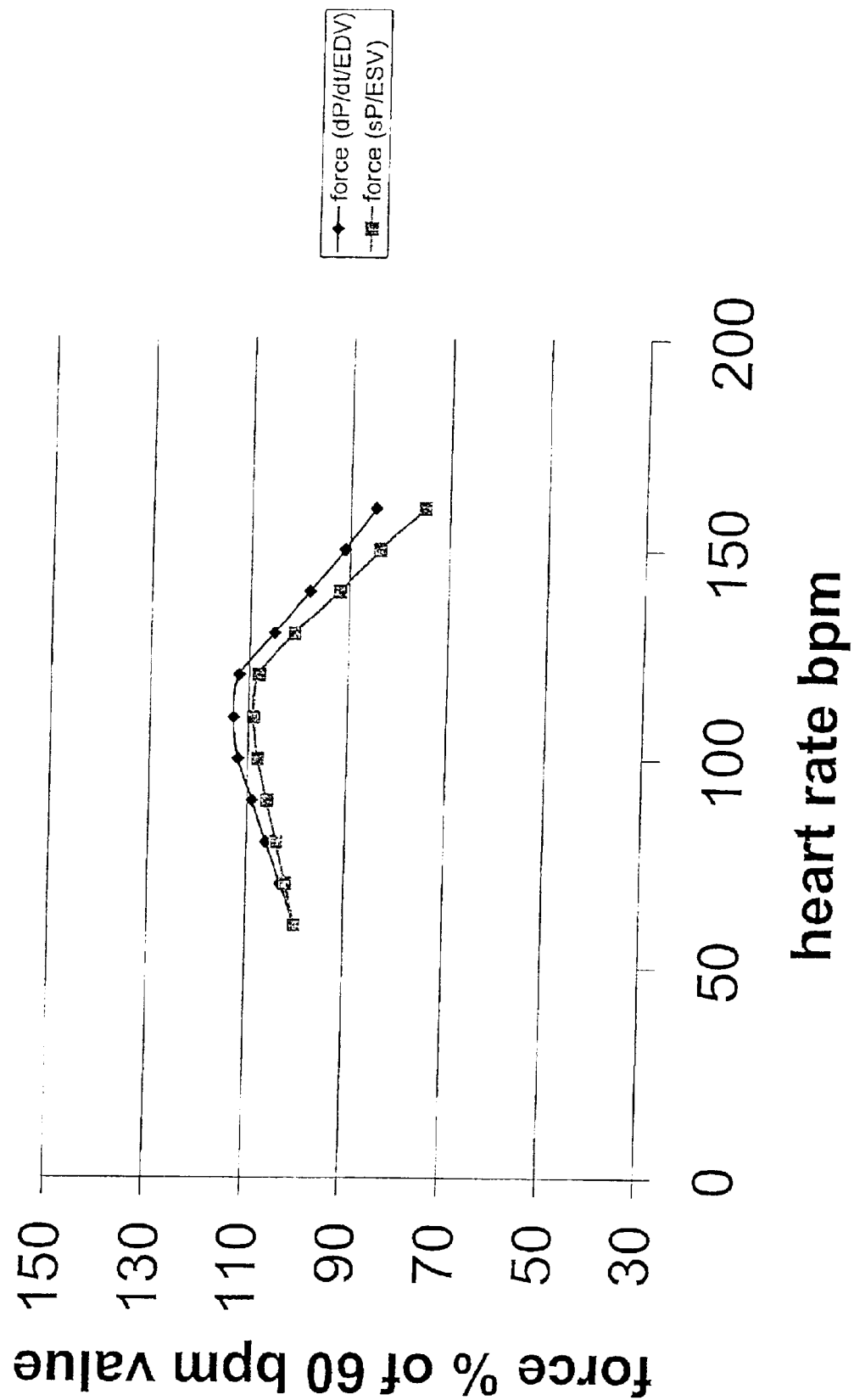

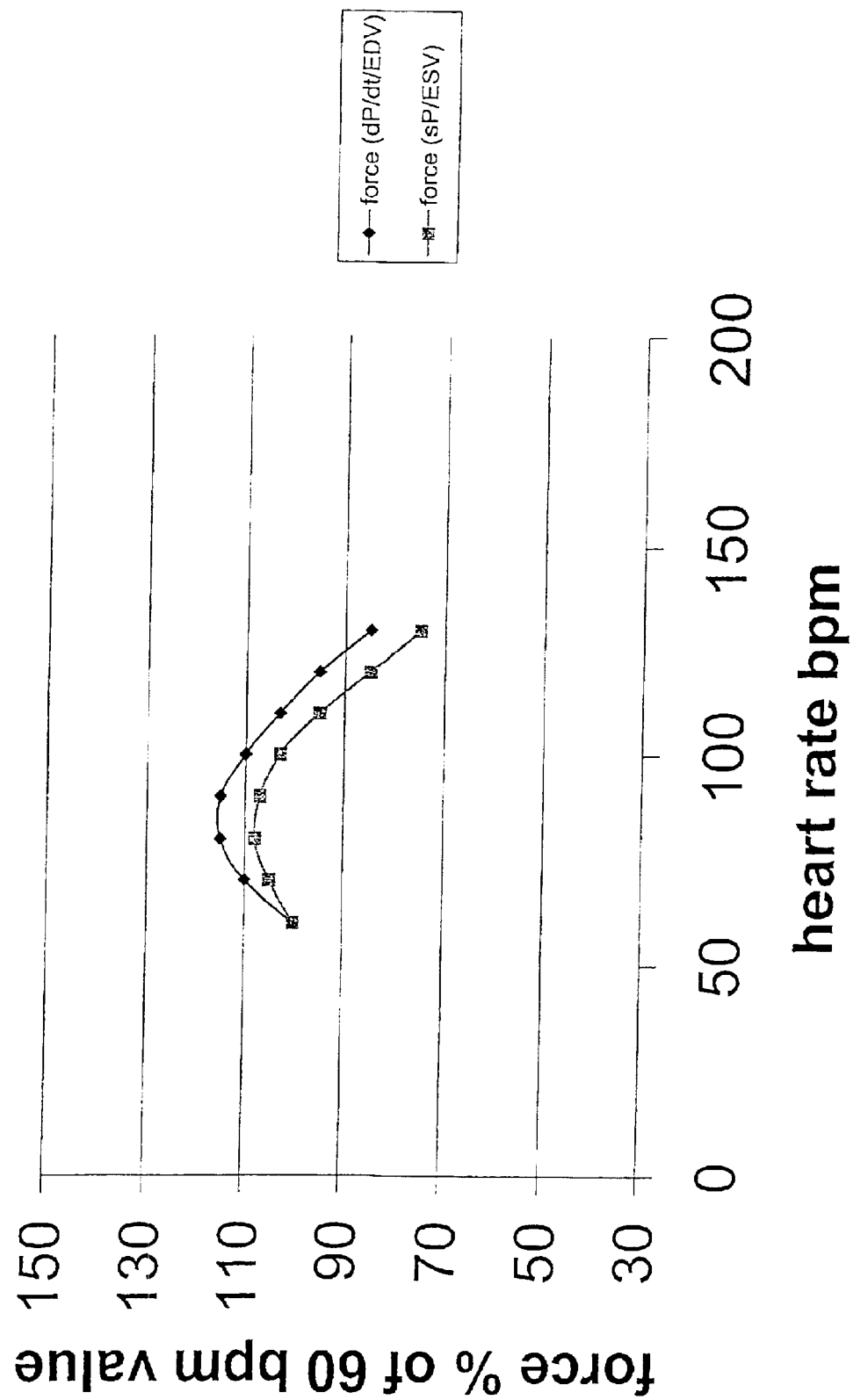

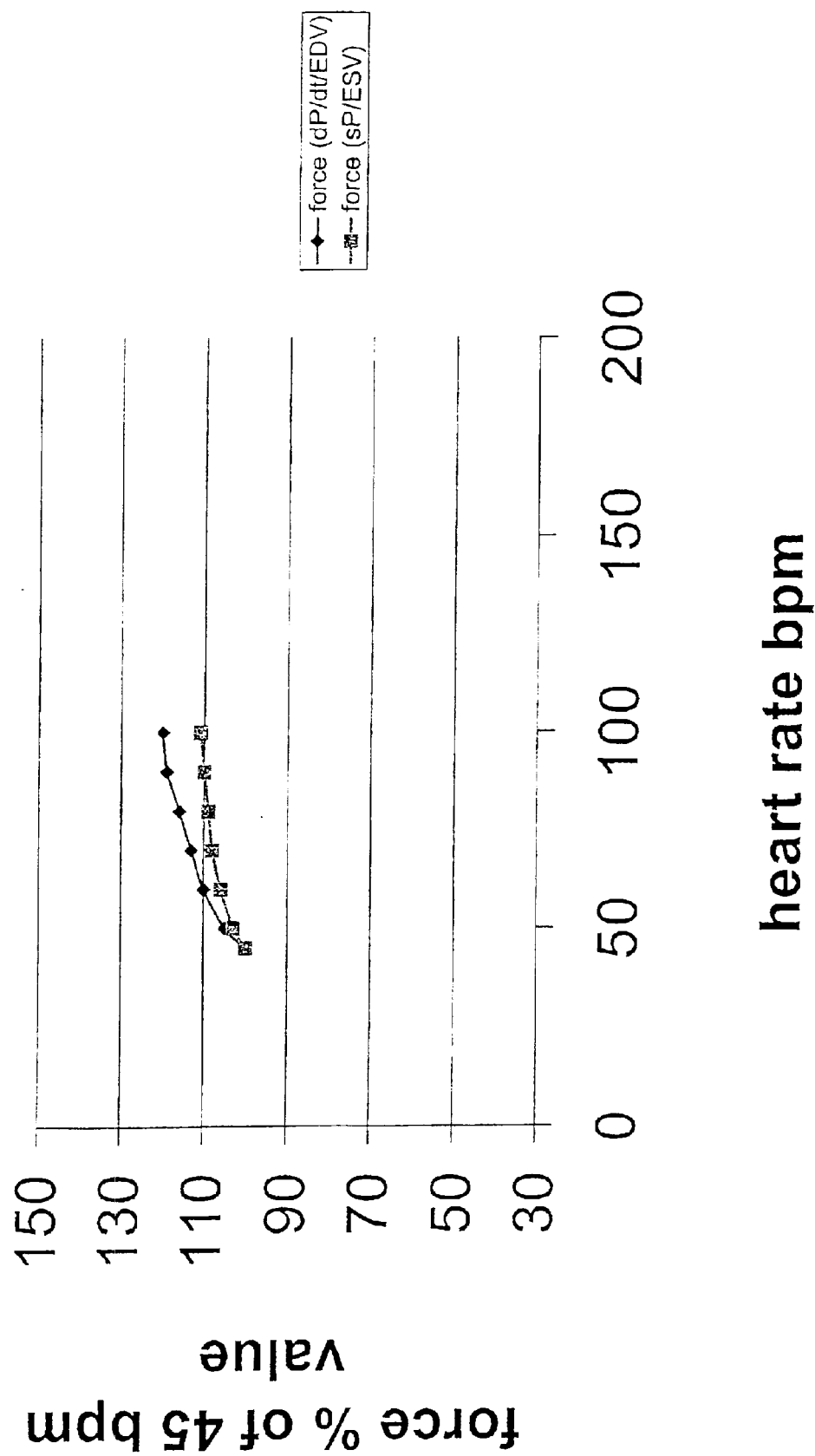
Fig. 5 Dilated cardiomyopathy (beta blockers on)

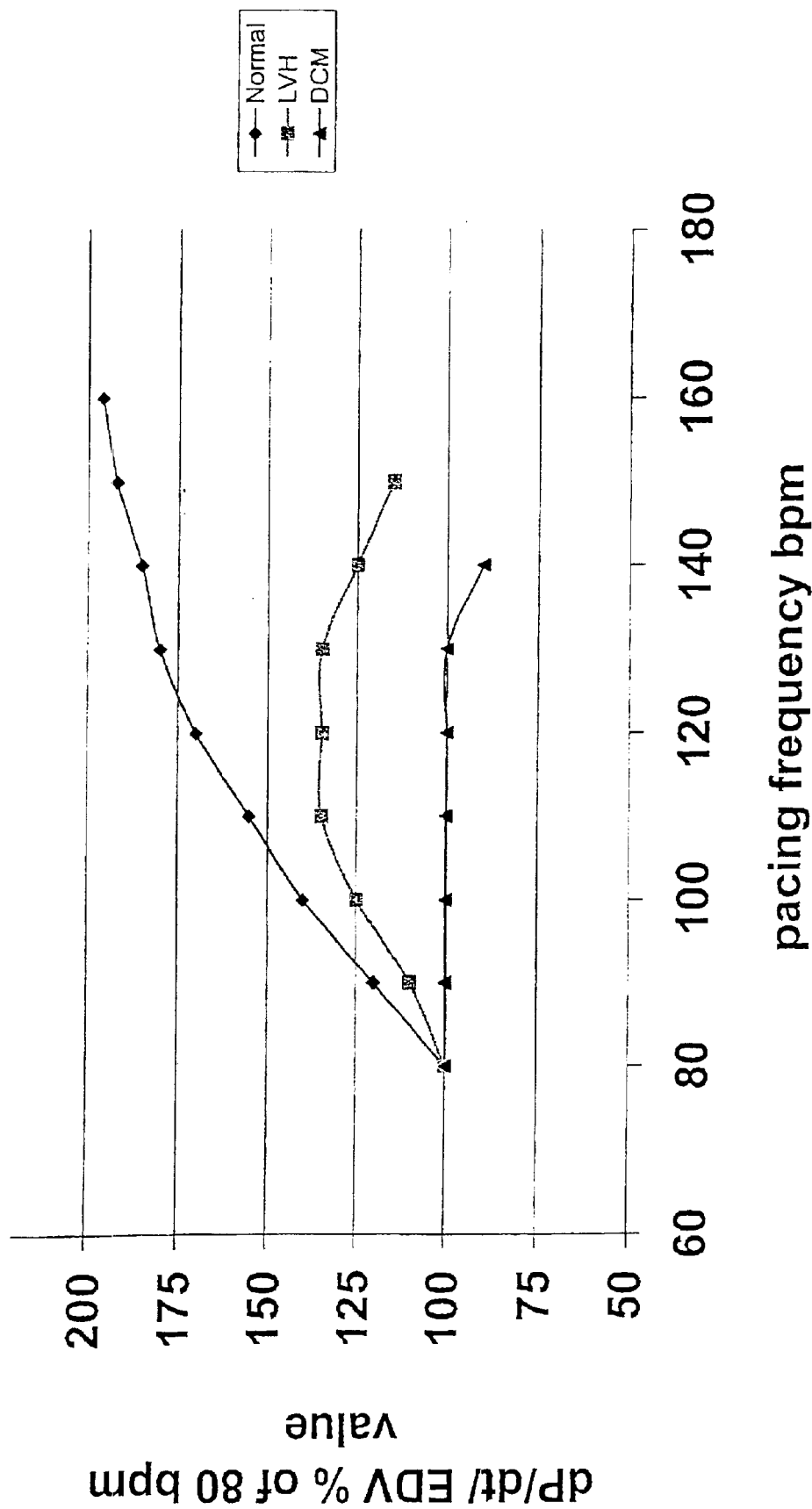
Fig. 6 - Increase in heart rate produced by pacing in resting patients

METHOD AND DEVICE FOR THE DIAGNOSIS AND THERAPY OF CHRONIC HEART FAILURE

TECHNICAL FIELD

The invention relates generally to a method and the relative apparatus for monitoring the physiological conditions of a patient, with particular reference to cardiovascular function in the presence of chronic heart failure.

In particular the invention comprises a device incorporating a microprocessor, a memory and a system for monitoring the ventricular function, from which certain diagnostic information and the relative therapeutic options may derive.

The ventricular function is monitored together with the heart rate to establish the individual force-frequency relationship of the patient. In the following the terms heart rate and heart frequency have the same meaning.

BACKGROUND ART

An increased heart rate progressively increases the contractile force of the heart (Bowditch phenomenon). In this respect, in a normal heart the influx of calcium through the calcium channels is normally increased by high heart rate.

In humans, an increase in heart rate from 60 to 170 beats per minute stimulates developed force.

When the heart rate exceeds 170 beats per minute, the force developed by the ventricle begins to decrease.

If chronic heart failure and/or myopathic, valvulopathic or ischemic cardiomyopathy is present, this intrinsic property of the myocardium is partially or totally depressed, because of which the contractile force decreases for cardiac frequencies of the order of 100 bpm or even lower. The decompensated myocardium undergoes a phenotypic change with activity alteration of the enzymes which regulate calcium homeostasis: diastolic uptake and systolic release of calcium decrease and contractile performance improves only with bradycardia.

The heart rate starting from which the contractile force begins to decline diminishes progressively for known pathologies such as ischemic cardiomyopathy, diabetic cardiomyopathy, mitral regurgitation and dilated cardiomyopathy.

The optimum contraction rate, i.e. the rate corresponding to the strongest contractile force, varies for each pathology, for each different stage of the illness, and for each patient.

In these pathologies a decrease in the capacity of the ventricles to adapt to the greater requirement occurs, this decrease sometimes being defined as loss of ventricular pumping reserve; the contractile reserve loss is unable to support the increase in the function requirement which occurs during exercise.

It therefore happens that when pathologies are present, a compensated system, in which the greater function requirement is satisfied naturally by a positive force-frequency relationship, passes to a decompensated or unstable system, in which the force-frequency relationship is depressed, flattened or negative, i.e. the system responds to a disturbing event by amplifying the effect of the disturbance, and hence becomes unstable.

The deterioration and the possible inversion of the myocardial force-frequency relationship is a mechanism of conversion from a compensation situation to a cardiac decompensation situation in a diseased heart.

In advanced conditions of chronic heart failure the peak of the force-frequency relationship is sufficiently displaced towards low frequencies to produce a flattened or a negative slope on the rate spectrum between 80 and 160 beats per minute (bpm), which in practice is the entire spectrum of the chronic heart failure patient. This decrease in force as soon as the heart rate increases means that a sudden rate increase predisposes the ventricles to dilation because of venous overloading with increase in telediastolic pressure. Different therapies are known for remedying chronic heart failure, aimed at reducing heart rate to remedy the decrease in force with increase in rate, however the response of the individual therapies must be adapted to the particular conditions of the patient.

For example, therapy with beta blockers has proved effective in cardiomegaly regression and in improving the myocardial function in patients suffering from dilated cardiomyopathy, however patients do not respond uniformly to this therapy.

Because of the pejorative effect of inversion of the force-frequency relationship, one of the effectiveness components of therapy with beta blockers derives from the reduction in heart rate in itself.

If the bradycardia is sufficient to reposition the spectrum of heart operative frequencies to sufficiently low levels, the negative part of the force-frequency relationship is avoided.

The bradycardic action of beta blockers reduces the number of daily working phases of the heart in the negative part of the force-frequency relationship.

As the flattening and the descending limb of the force-frequency curve appears at different frequencies in the different types of cardiac decompensation and in different patients, the effectiveness of the action of beta blockers is variable.

To optimize chronic heart failure therapy, it therefore appears essential to identify in each patient the ascending part of the force-frequency curve and the specific rate which when exceeded initiates the flattening and the descending part, in order to optimize individual therapy for chronic heart failure.

The subsequent therapeutic action in an individual patient will be more advantageous the closer the negative part of the force-frequency curve lies to the basal heart rate.

DISCLOSURE OF THE INVENTION

The present invention generally concerns a method and relative apparatus for determining the force-frequency relationship of an individual for the purpose of recognizing and/or avoiding chronic heart failure.

The force-frequency relationship regions are initially identified to define the normality and abnormality components of an individual patient.

These regions automatically change in response to a decompensation phase or the absence thereof. The normality and abnormality limits of the force-frequency relationship adapt specifically to the physiological and cardiological conditions of the individual patient.

When a decompensation phase occurs, the sequence which led to the decompensation phase is memorized.

The force-frequency relationship is then compared with the sequence which led to the decompensation phase to anticipate its reoccurrence.

The invention provides a system comprising a microprocessor which from the heart receives informative signals concerning the force-frequency relationship of the patient.

The system records the points of the force-frequency relationship by successive beats from which it then derives a diagram of the force-frequency relationship over predetermined time periods.

The apparatus then compares the points of the force-frequency relationship with the memorized regions of the force-frequency relationship in which the normal and abnormal regions are defined.

If the point on the force-frequency relationship is within an abnormal region of the force-frequency relationship, specific provisions are adopted or an appropriate therapeutic regime is initiated. If instead the point on the force-frequency relationship is within a normal region of the force-frequency relationship, no specific provision is necessary.

However, if the point on the force-frequency relationship is within a normal region of the force-frequency relationship but the patient is in any event experiencing a decompensation situation, an appropriate therapeutic regime can be initiated.

The definition of abnormality or normality of the force-frequency relationship changes depending on the particular physiopathological conditions of an individual.

If a worsening of chronic heart failure occurs, a memory permanently memorizes it as an item of timed data plus a series of timed data leading up to the worsening.

Overall this series of timed data provides a definition of passage from the generally normal component of the force-frequency relationship to the generally abnormal component of the force-frequency relationship.

This passage enables a future worsening of chronic heart failure to be predicted and to identify a current phase of worsening of chronic heart failure.

This comparison shows if the person is again experiencing an impelling condition of worsening of chronic heart failure.

As a further advantage, the abnormality region of the force-frequency relationship can be divided into a plurality of abnormal sub-regions. Each of these sub-regions corresponds to a therapeutic regime. In addition, the therapeutic regimes can have a structure which involves progressive increments of aggressiveness.

Additionally, the selective activation of the therapeutic regimes minimizes non-essential energy consumption and diagnostic activity, and hence conserves the life of the energy source.

Monitoring the patient's conditions not only enables his condition to be verified in terms of identifying an abnormal situation not in itself critical but predictive of a future worsening of chronic heart failure, but in particular enables the effectiveness of therapies to be verified and their influence on the patient's condition under conditions of normality.

In this respect, a sufferer from chronic heart failure can be in a negative slope phase of his force-frequency relationship only for a fraction of the 24 hours in a day, depending on his specific activity during certain periods of the 24 hours.

In other words, the sufferer can present a compensated behaviour in certain situations, for example when seated or walking slowly, but decompensation if climbing stairs, running or performing certain activities.

As distribution of the daily activities of the patient is variable, during the day the patient experiences, depending on the activities normally performed, periods in which his force-frequency relationship is of positive slope and periods in which his force-frequency relationship is of negative slope or flat.

Without altering his habitual way of life, the object of the therapy is to increase periods of compensation relative to periods of decompensation.

If for example the patient presents negative slope phases of his force-frequency relationship lasting a total of six hours in twenty-four, an effective therapy would decrease the total duration of the negative slope phases, whereas an unsuitable therapy would increase the total duration of the negative slope phases.

Known check up systems do not enable therapy effectiveness to be verified other than by occasional checks on the patient under rest conditions.

Therapy effectiveness is verified by checking only the resting points of the force-frequency curve.

Any therapy correction made on the basis of these checks is therefore often untimely.

By monitoring in accordance with the invention, not only can positive or negative decompensation changes as a result of certain events be determined, but also the variation in the force-frequency curve over twenty-four hours.

A three-dimensional diagram is hence determined which for each heart rate not only indicates the instantaneous force value but also enables the variation of said value with time to be monitored.

If the curve of force variation at a determined heart rate during the course of the day is reproduced as a two-dimensional diagram, it gives a continuous indication of the progress of decompensation situations in response to the therapies adopted.

According to the invention, the force information is derived from intracardiac pressure curves, or from peripheral pressure curves, or from ventricular volumes, or from the pressure/volume relationships, or from cardiac tone, or via impedance, or by Doppler flow measurement, or by echo-Doppler, or by a combination of all the described parameters, or by each combination of the described parameters.

The invention comprises a data processing circuit incorporated into the apparatus to receive internal or subcutaneous or external ECG electrical signals.

The circuit output can be fed to an analog/digital converter under the control of a microprocessor to convert the signals to digital data.

Associated with the microprocessor there is a memory for memorizing the digital data in ordered manner, which memorized data can be also read remotely by a telemetric connection.

The apparatus, comprising a microprocessor, can be programmed to initiate data memorization when a decompensation phase arises.

The microprocessor which controls the apparatus operation also comprises a memory containing an instruction program to be executed by the microprocessor.

The memory is suitable for storing digital information reaching it from an analog/digital conversion module.

The invention also comprises the apparatus for implementing the method, the essential characteristics of which are defined in the claims.

According to the invention, at least one sensor emitting ventricular force-indicative signals deriving from direct or indirect measurements thereof is associated with an ECG sensor arranged to measure cardiac electrical activity and to emit electrical signals indicative thereof.

Said signals emitted by said sensors are transformed from analog to digital by known means, and fed to a processor which processes them to obtain a force-frequency curve, and the variations thereof with time.

The sensors which emit signals indicative of the ventricular force are chosen from one or more of the following, possibly in combination.

Said sensors can comprise an intracardiac or external pressure sensor, or an external or internal ventricular volume sensor of the type known to the expert of the art, or the combination of a pressure sensor and a volume sensor.

There can also be provided an internal or external sensor for sensing cardiac force of contraction and/or the rate of tension development (cardiac tone and/or calcium transient), or an impedance measurement sensor of known type.

A Doppler sensor can also be used consisting of one or more piezoelectric crystals which determine:

cardiac output stroke volume diastolic mitral flow measurement and systolic mitral regurgitation flow measurement mitral regurgitation curve and dP/dt derivative E wave deceleration time mitral A wave duration and duration of pulmonary venous regurgitation AR wave during atrial contraction, to establish relative A wave and AR wave duration.

It is sometimes convenient to use an implanted or external echo sensor consisting of one or more piezoelectric crystals which determine the dimensions of the cardiac chambers during the cardiac cycle.

The echo sensor and the Doppler sensor are sometimes used in combination, they consisting of one or more piezoelectric crystals for the combined determination of the intracardiac flow signals and the dimensions of the cardiac chambers.

The following examples, illustrated by the accompanying drawings, provide a better understanding of the invention.

EXAMPLE 1

Illustrated in FIG. 1

Normal subject.

X-axis: heart rate bpm, (beats per minute)

Y-axis: ventricular force expressed as dP/dt/EDV= maximal rate of left ventricular pressure development divided by end-diastolic volume (EDV) or expressed as sP/ESV=left ventricular end-systolic pressure volume ratio (end-systolic ventricular pressure divided by the end-systolic volume).

Values of ventricular force in each plot are normalized with respect to the corresponding value at 60 bpm.

During progressive physical activity, in the physiological rate range between 60 and 180 bpm, the force-frequency relationship is constantly ascending. The slope of the sP/ESV curve is less than the slope of the dP/dt/EDV curve.

EXAMPLE 2

Illustrated in FIG. 2

Diabetic cardiomyopathy.

X-axis: heart rate bpm, (beats per minute)

Y-axis: ventricular force expressed as dP/dt/EDV= maximal rate of left ventricular pressure development divided by end-diastolic volume (EDV) or expressed as sP/ESV=left ventricular end-systolic pressure volume ratio (end-systolic ventricular pressure divided by the end-systolic volume).

Values of ventricular force in each plot are normalized with respect to the corresponding value at 60 bpm.

The force-frequency relationship within the rate range between 60 and 170 bpm is described by a curve which ascends between 60 and 110 bpm, is flat between 110 and 130 bpm, and descends between 130 and 170 bpm.

For frequencies higher than 130 bpm the cardiac intropism (dP/dt) decreases with increasing end-diastolic volume of the left ventricle (EDV); simultaneously the systolic pressure (sP) decreases and the left ventricle lowerly empties during systole (with increase in ESV).

EXAMPLE 3

Illustrated in the Accompanying FIG. 3

Mitral regurgitation.

X-axis: heart rate bpm, (beats per minute)

Y-axis: ventricular force expressed as dP/dt/EDV= maximal rate of left ventricular pressure development divided by end-diastolic volume (EDV) or expressed as sP/ESV=left ventricular end-systolic pressure volume ratio (end-systolic ventricular pressure divided by the end-systolic volume).

Values of ventricular force in each plot are normalized with respect to the corresponding value at 60 bpm.

The force-frequency relationship within the rate range between 60 and 160 bpm is described by a curve which ascends between 60 and 110 bpm, is flat between 100 and 120 bpm, and descends between 120 and 160 bpm. The force of the force-frequency relationship increases modestly between 60 and 100 bpm. For frequencies higher than 120 bpm the decrease in ventricular force is consistent and for frequencies higher than 130 bpm the value is less than basal. This event corresponds clinically to exertional dyspnea typical of this pathology.

EXAMPLE 4

Illustrated in the Accompanying FIG. 4

Dilated cardiomyopathy.

X-axis: heart rate bpm, (beats per minute)

Y-axis: ventricular force expressed as dP/dt/EDV= maximal rate of left ventricular pressure development divided by end-diastolic volume (EDV) or expressed as sP/ESV=left ventricular end-systolic pressure volume ratio (end-systolic ventricular pressure divided by the end-systolic volume).

Values of ventricular force in each plot are normalized with respect to the corresponding value at 60 bpm.

The peak of the force-frequency relationship is sufficiently displaced towards low frequencies to have a negative slope over the almost entire range of frequencies in vivo (between 80 and 150 bpm). The reduction in contractile force as soon as the heart rate increases predisposes the ventricle to dilation because of venous overloading with increase in end-diastolic pressure. Because of the pejorative effect of inversion of the force-frequency relationship, a therapy is advisable which decreases heart rate.

EXAMPLE 5

Illustrated in the Accompanying FIG. 5

The dilated cardiomyopathy of Example 4 during therapy with beta blockers.

X-axis: heart rate bpm, (beats per minute)

Y-axis: ventricular force expressed as dP/dt/EDV= maximal rate of left ventricular pressure development divided by end-diastolic volume (EDV) or expressed as sP/ESV=left ventricular end-systolic pressure volume ratio (end-systolic ventricular pressure divided by the end-systolic volume).

Values of ventricular force in each plot are normalized with respect to the corresponding value at 45 bpm.

The bradycardia induced by the beta blocking therapy was sufficient to reposition the operative range of the heart at low rate levels (between 50 and 100 bpm), and the negative part of the force-frequency relationship is avoided.

The same therapeutic result is obtained in a subject not in spontaneous heart rate when electrically stimulated while maintaining the pacing rate between 50 and 100 beats per minute.

EXAMPLE 6

Illustrated in FIG. 6

Increase in heart rate produced by pacing in resting patients.

X-axis: pacing frequency bpm, (beats per minute)

Y-axis: ventricular force expressed as dP/dt/EDV= maximal rate of left ventricular pressure development divided by end-diastolic volume (EDV).

Values of ventricular force in each plot are normalized with respect to the corresponding value at 80 bpm.

Increase in heart rate produced by pacing in non-exercising subjects to assess the force-frequency relationship at rest. Pacing was initiated at 80 bpm and increased in definite increments up to peak pacing rate (peak pacing rate=the heart rate at which either second-degree atrioventricular block or pulsus alternans occurred). Cardiac output remains constant despite the pacing induced tachycardia, and the end-diastolic volume diminishes as pacing frequency increases.

Patient 1: the heart is normal (Normal) and the slope of the force-frequency relationship is positive.

Patient 2: a case with severe left ventricular hypertrophy (LVH). The force-frequency relationship is biphasic, with an initial positive slope (ascending limb), and subsequent negative slope (descending limb). Critical heart rate is between 100 and 130 bpm.

Patient 3: a case with dilated cardiomyopathy (DCM) exibited a flat force-frequency relationship with a descending limb at higher frequencies.

What is claimed is:

1. A method for the diagnosis and therapy of chronic heart failure comprising continuous monitoring of the patient and continuous determination of significant decompensation parameters during a sample period of normal patient life, recording the data determined, continuously monitoring these data during therapy, comparing the memorized data with those determined during the same time span of the sample period and comparing the duration of periods in which decompensation is present with the total duration of those periods during which decompensation is absent or conforms to that determined during the sample period, wherein the memorized parameters comprise the curve of ventricular contractile force variation as a function of heart rate.

2. A method as claimed in claim 1, wherein the memorized parameters are the heart rate, the ventricular contractile force, and the curve of force variation as a function of heart rate.

3. A method as claimed in claim 2, wherein the memorized parameters are the heart rate, the ventricular contractile force, and the curve of force variation as a function of heart rate at determined moments of the sample period.

4. A method as claimed in claim 2, in which memorizing the force-frequency curve variations occurs at least during a period equal to the sample period.

5. A method as claimed in claim 2, deriving the force data from the intracardiac pressure curves.

6. A method as claimed in claim 2, deriving the force data from the peripheral pressure curves.

7. A method as claimed in claim 2, deriving the force data from the ventricular volumes.

8. A method as claimed in claim 2, deriving the force data from the pressure/volume relationship.

9. A method as claimed in claim 2, deriving the force data from cardiac tone (force of contraction and/or rate of tension development).

10. A method as claimed in claim 2, deriving the force data via impedance.

11. A method as claimed in claim 2, deriving the force data from Doppler flow measurement.

12. A method as claimed in claim 2, deriving the force data with echo-Doppler.

13. A method as claimed in claim 2, deriving the force data from a combination of all or part of the following parameters: the intracardiac pressure curves, the peripheral pressure curves, the ventricular volumes, the pressure/volume relationship, the cardiac tone, the impedance, the Doppler flow measurement, the echo-Doppler measurement.

14. A method as claimed in claim 2, expressing the ventricular force as dP/dt/EDV, which indicates the maximal rate of left ventricular pressure development divided by end-diastolic volume (EDV).

15. A method as claimed in claim 2, expressing the ventricular force as sP/ESV, which indicates the left ventricular end-systolic pressure volume ratio (end-systolic ventricular pressure divided by the end-systolic volume).

* * * * *